United States Patent [19]

Löfroth et al.

[11] Patent Number: 5,795,896
[45] Date of Patent: Aug. 18, 1998

[54] ANTITHROMBOTIC FORMULATION, PROCESS FOR ITS MANUFACTURING, AND USE THEREOF

[75] Inventors: Jan-Erik Löfroth, Mölndal; Anna-Lena Ungell, Göteborg, both of Sweden

[73] Assignee: Astra Aktiebolag, Sodertalje, Sweden

[21] Appl. No.: 564,122

[22] PCT Filed: Nov. 29, 1995

[86] PCT No.: PCT/SE95/01425

§ 371 Date: Dec. 18, 1995

§ 102(e) Date: Dec. 18, 1995

[87] PCT Pub. No.: WO96/16671

PCT Pub. Date: Jun. 6, 1996

[30] Foreign Application Priority Data

Dec. 2, 1994 [SE] Sweden ................... 9404196

[51] Int. Cl.$^6$ ............................ A61K 31/505
[52] U.S. Cl. ............................ 514/256
[58] Field of Search ................... 514/256

[56] References Cited

U.S. PATENT DOCUMENTS

| | | |
|---|---|---|
| 4,346,078 | 8/1982 | Bajusz et al. . |
| 4,568,636 | 2/1986 | Svendsen ............... 435/13 |
| 4,703,036 | 10/1987 | Bajusz et al. . |
| 4,977,168 | 12/1990 | Bernat et al. . |
| 5,037,819 | 8/1991 | Han ............... 514/210 |
| 5,110,812 | 5/1992 | Han ............... 514/210 |
| 5,187,157 | 2/1993 | Kettner et al. . |
| 5,260,307 | 11/1993 | Ackermann et al. . |

FOREIGN PATENT DOCUMENTS

| | | |
|---|---|---|
| 0074787 | 3/1983 | European Pat. Off. . |
| 0192135 | 3/1986 | European Pat. Off. . |
| 0195212 | 9/1986 | European Pat. Off. . |
| 0235692 | 9/1987 | European Pat. Off. . |
| 0293881 | 6/1988 | European Pat. Off. . |
| 0362002 | 4/1990 | European Pat. Off. . |
| 0364344 | 4/1990 | European Pat. Off. . |
| 0479489 | 9/1991 | European Pat. Off. . |
| 0468231 | 1/1992 | European Pat. Off. . |
| 0471651 | 2/1992 | European Pat. Off. . |
| 0513543 | 11/1992 | European Pat. Off. . |
| 0530167 | 3/1993 | European Pat. Off. . |
| 0542525 | 5/1993 | European Pat. Off. . |
| 2085444 | 4/1982 | United Kingdom . |
| 9204371 | 3/1992 | WIPO . |
| 9208709 | 3/1992 | WIPO . |
| 9207869 | 5/1992 | WIPO . |

OTHER PUBLICATIONS

Jackson et al. "Pharmacological Assessment of the Antithrombotic Activity of the Peptide Thrombin Inhibitor ... ", J. of Pharm. Exp. Ther. 261: 546–552, 1992.

Knabb et al. "In Vivo Characterization of a New Synthetic Thrombin Inhibitor", Thrombosis and Haemostasis, 67(1): 56–59, 1992.

Bajusz et al. "Inhibition of Thrombin with H–and Boc–D–Phe–Pro–Agm," Chem. Abs. 99: 205609w, 1983.

Klement et al. "The Effect of Thrombin Inhibitors on Tissue Plasminogen Activator Induced Thrombolysis in a Rat Model", Thrombosis and Haemostasis, 68(1): 64–68, 1992.

Märki et al., "The Anticoagulant and Antithrombotic Properties of Hirudins", Thrombosis and Haemostasis, 64(3): 344–348, 1990.

Broersma et al., "The Effect of Thrombin Inhibition in a Rat Arterial Thrombosis Model", Thrombosis Research, 64:405–412, 1991.

Persson et al. Thorax 47: 993–1000, 1992.

Salomonson et al. Am. Rev. Resp. Dis. 146: 1535–1542, 1992.

Markwardt et al. Biochem. Pharm. 23: 2247–2256, 1974.

Malek et al. "Palladium–catalyzed synthesis of Cinnamylamides", J. Org. Chem. 47(27):5395–5397, 1982.

Malek, et al. Chem. Abs. 98: 16353, 1983.

Chung et al. J. Organic Chem. 1: 270–275, 1990.

Glusa et al. "The influence of benzamidine derivaties on human platelet function," Thrombosis et Diathesis Haemorrhagica 31: 172–178, 1974.

Anderson and Lok, J. Organic Chem. 37: 3953, 1972.

Fareed et al., Ann. N.Y. Acad. Sci. 370:765–784, 1981.

Geratz, J.D. "Inhibition of thrombin, plasmin and plasminogen compounds," Thrombosis et Diathesis Halemorrhagica 23(3), 486–499, 1970.

*Primary Examiner*—Keith MacMillan
*Attorney, Agent, or Firm*—Nixon & Vanderhye

[57] ABSTRACT

A new pharmaceutical formulation comprising the thrombin inhibitor HOOC—CH$_2$—(R)-Cgl-Aze-Pab in combination with one or more absorption enhancing agents, a process for the preparation of such a pharmacutical formulation, the use of such a formulation in the treatment of thromboembolism as well as a method of treating a patient in need of antithrombotic treatment and thromboembolism by using said formulation.

22 Claims, 1 Drawing Sheet

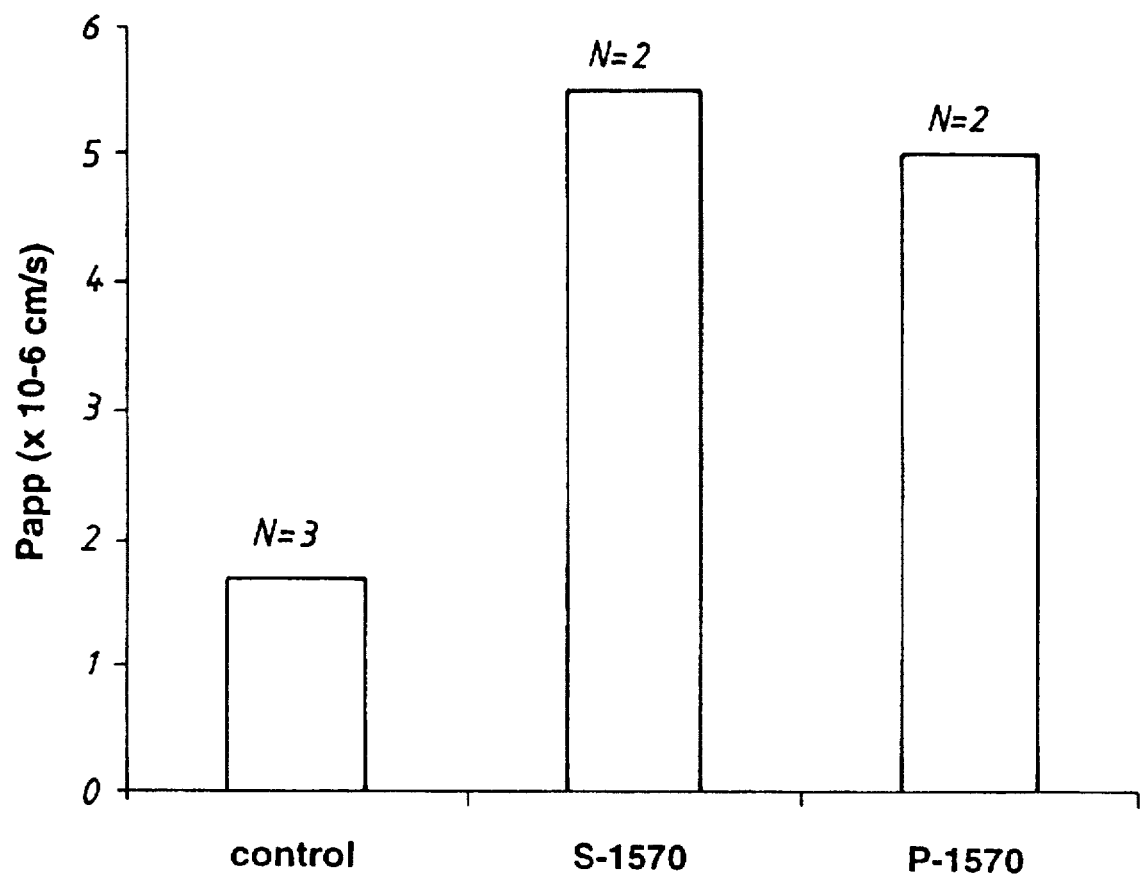

ANTITHROMBOTIC FORMULATION, PROCESS FOR ITS MANUFACTURING, AND USE THEREOF

FIELD OF THE INVENTION

The present invention relates to a new pharmaceutical formulation comprising the thrombin inhibitor HOOC—$CH_2$—(R)-Cgl-Aze-Pab in combination with one or more absorption enhancing agents, a process for the preparation of such a pharmaceutical formulation, and the use of such a formulation in the treatment of thromboembolism as well as a method of treating a patient in need of such a treatment by using said formulation.

BACKGROUND

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions; one of the final steps is conversion of the proenzyme prothrombin to the active enzyme thrombin.

Thrombin plays a central role in coagulation. It activates platelets, it converts fibrinogen into fibrin monomers, which polymerize spontaneously into filaments, and it activates factor XIII, which in turn crosslinks the polymer to insoluble fibrin. Thrombin further activates factor V and factor VIII in a positive feedback reaction. Inhibitors of thrombin are therefore expected to be effective anticoagulants by inhibition of platelet activation, fibrin formation and fibrin stabilization. By inhibiting the positive feedback mechanism such inhibitors are expected to exert inhibition early in the chain of events leading to coagulation and thrombosis.

Peptidic or peptide like thrombin inhibitors, like many other peptide-like substances, are prone to limited or variable absorption when administered. This is due to the influence of different barriers of metabolic and physical character, such as enzymatic degradation, tendencies toward complex formation with components from the formulation or the biological environment, limitations in transport possibilities etc. One object of the present pharmaceutical formulation is to facilitate for the active agent to overcome such barriers, and to obtain an enhanced and reproducible absorption of the active agent. Formulation components that have such influence and thus can help the active agent are called absorption enhancers.

Prior Art

Concerning the use of absorption enhancers in pharmaceutical formulations, several reports and reviews in the literature exist. Enhancing properties have been reported of different types of substances, such as surface active agents and lipids, chelators, and polymers. Comprehensive reviews have been presented by E J van Hoogdalem et al., Pharmac Theor vol 44, 407–443 (1989), by S Muranishi, Crit Rev Ther Drug Carrier Syst vol 7, 1–33 (1990), by E S Swenson and W J Curatolo, Adv Drug Deliv Rev vol 8, 39–92 (1992), and in Drug Absorption Enhancement (Ed.: A B G de Boer), Harwood Academic Publishers 1994.

DISCLOSURE OF THE INVENTION

It has been found that the absorption of the therapeutically active thrombin inhibitor HOOC—$CH_2$—(R)Cgl-Aze-Pab can be modified by incorporating enhancing agents in the pharmaceutical formulations containing said therapeutically active compound.

Therefore, an object of the present invention is to provide novel pharmaceutical formulations comprising the thrombin inhibitor HOOC—$CH_2$—(R)-Cgl-Aze-Pab in combination with one or more absorption enhancing agents and optionally a pharmaceutically acceptable carrier, and a process for the preparation of such pharmaceutical formulations.

Means of obtaining improved formulations of this therapeutically active drug are based on the use of absorption enhancing agents, such as, but not limited to, surface active agents, lipids, other drugs and polymers to obtain positive effects which result in an enhanced and/or less variable absorption of the therapeutically active agent when said agent is given by different administration routes, such as oral, rectal, buccal, nasal, pulmonary, inhalation route etc., and combinations of such agents to obtain even positive synergistic effects which result in even higher enhanced absorption.

The absorption enhancing effects described in this invention are meant to be obtained by one or more additives in the formulation, such as, but not limited to:

Non-steroidal anti-inflammatory drugs and derivatives, such as sodium salicylate, sodium 5-methoxysalicylate, indomethacin and diclofenac;

Surfactants, such as nonionic surfactants, e.g., sorbitan esters (Span series), polysorbates (Tween series), poloxyethylated glycol monoethers (like the Brij series), polyoxylated alkyl esters (Myrj series), polyoxyethylated alkyl phenols (like the Triton series), alkyl glucosides like sugar glycosides, e.g., dodecylmaltoside, sugar fatty acid esters, e.g., sucrose laurate, sucrose monostearate etc and saponins;

ampholytic surfactants, e.g., betaines;

anionic surfactants, e.g., sulphated fatty alcohols, sulphated polyoxyethylated alcohols, others like dioctyl sulphosuccinate;

cationic surfactants, e.g., ammonium compounds. Bile salts, such as dihydroxy bile salts like sodium deoxycholate, trihydroxy bile salts like sodium glycocholate and fusidates, e.g., sodium dihydrofusidate;

Soaps and fatty acids, and their salts, e.g. octanoic acid, decanoic acid and sodium decanoate;

Lipids, such as glycerides, e.g., glycerylmonooctanoate and glycerylmonoolein;

phospholipids, e.g., DPPC and DMPC;

Oils, e.g., soy bean oil and sunflower oil;

Enamines, such as DL-phenylanaline and ethylacetoacetate enamine;

Chelating agents, e.g., EDTA, EGTA, and citric acid;

Phenothiazines, such as chlorpromazine;

Fatty acid derivatives of carnitine and peptides, e.g., palmitoyl-DL-carnitine and N-myristoyl-L-propyl-L-prolyl-glycinate;

Other substances, e.g., azone, concanavalin A, phosphate and phosphonate derivatives such as DL-α-glycerophosphate and 3-amino-1-hydroxypropylidene-1,1-diphosphonate, diethyl maleate and diethylethoxymethylene malonate;

Products from Maillard reactions, e.g., compounds from a glucoselysine reaction;

Polymers, such as polyacrylic acids, e.g., Carbopol®, polycarbophil; chitosan and chitosan derivatives; and block copolymers, e.g., poloxamers, poloxamines, and meroxapols.

3

Suitable intended combinations of the enhancing agents are, but are not limited to:

Lipids and bile salts, e.g., monoolein and sodium taurocholate;

Lipids and phospholipids, e.g., medium chain glycerides and lecithins;

Surfactants and oils, e.g., sucrose fatty acid esters and soy bean oil; and

Polymers and lipids, e.g., polycarbophil and monoolein.

The dosage form used may be a solid, semisolid or liquid preparation prepared by known techniques. Usually the active substance will constitute between 0.1 and 99% by weight of the preparation, more specifically between 0.1 and 50% by weight for preparations intended for parenteral administration and between 0.2 and 90% by weight for preparations suitable for oral administration.

Suitable daily doses of the therapeutically active drug in therapeutical treatment of humans are about 0.001–100 mg/kg body weight at peroral administration and 0.001–50 mg/kg body weight at parenteral administration.

The enhancing agent, or combinations of enhancing agents, will constitute between 0.1 and 99% by weight of the preparation. The formulations thus obtained will increase the absorption and/or minimize the variability of the absorption of the theraputically active drug by different mechanisms.

The pharmaceutical formulations of the present invention comprising the modified dipeptide HOOC—$CH_2$—(R)Cgl-Aze-Pab and the absorption enhancing agents are intended for prophylaxis and treatment in arterial as well as venous thromboembolism.

Another object of the invention is a process for the manufacturing of said pharmaceutical formulation comprising adding the absorption enhancing agents to a solution of a therapeutically active compound HOOC—$CH_2$—(R)Cgl-Aze-Pab, optionally adjusting the pH with a buffering agent to a therapeutically acceptable pH, for instance between 5 to 9, preferably between 7 and 8, e.g. 7.4 and mixing all ingredients. The buffering agent may be a phosphate buffer such as $K_2HPO_4$ : $Na_2HPO_4$. Other ingredients conventionally used in pharmaceutical formulations such as carriers, isotonic agents such as NaCl known by a skilled person in the art may also be added to the pharmaceutical formulation of the present invention.

BRIEF DESCRIPTION OF THE DRAWINGS

FIG. 1 shows the effect of two absorption enhancing agents on the permeability of the intestinal membrane to HOOC—$CH_2$—(R)Cgl-Aze-Pab.

DETAILED DESCRIPTION OF THE INVENTION

The following description is illustrative of aspects of the invention.

Experimental Part

General experimental Procedures

Mass spectra were recorded on a Finnigan MAT TSQ 700 triple quadropole mass spectrometer equipped with an electrospray interface.

The $^1H$ NMR and $^{13}C$ NMR measurements were performed on BRUKER AC-P 300 and BRUKER AM 500 spectrometers, the former operating at a $^1H$ frequency of 500.14 MHz and a $^{13}C$ frequency of 125.76 MHz and the latter at $^1H$ and $^{13}C$ frequency of 300.13 MHz and 75.46 MHz respectively.

4

The samples were about 10–50 mg dissolved in 0.6 ml of one of the following solvents; $CDCl_3$ (isotopic purity>99.8%), $CD_3OD$ (isotopic purity (isotopic purity >99.98%). All solvents were purchased from Dr. Glaser AG, Basel.

The $^1H$ and $^{13}C$ chemical shift values in $CDCl_3$ and $CD_3OD$ are relative to tetramethylsilane as an external standard. The $^1H$ chemical shifts in $D_2O$ are relative to the sodium salt of 3-(trimethylsilyl)-$d_4$-propanoic acid and the $^{13}C$ chemical shifts in $D_2O$ are referenced relative to 1,4-dioxane (67.3 ppm), both as external standard. Calibrating with an external standard may in some cases cause minor shift differences compared to an internal standard, however, the difference in $^1H$ chemical shift is less than 0.02 ppm and in $^{13}C$ less than 0.1 ppm.

The $^1H$ NMR spectrum of peptide sequences containing a proline or a"proline like" residue frequently exhibits two sets of resonances. This corresponds to the existence of two contributing conformers with respect to the rotation around the amide bond, where proline contains the N-part of the amide bond. The conformers are named cis and trans. In the compounds containing such sequences the sequences (R)Cha-Aze- and (R)Cha-Pic- often give rise to a cis-trans equilibrium with one conformer as the preponderant conformer (>90%). In those cases only the $^1H$ chemical shifts of the major rotamer are reported. Only in the cases where the signals of the minor rotamer are clearly resolved are they reported in the NMR documentation. The same criterion is valid for the NH-signals in $CDCl_3$, only in the cases where the signals are clearly resolved are they reported in the NMR-documentation. This implies that the number of protons reported for some of the intermediates is less than the number of protons expected from the chemical formula.

Flash chromatography was carried out on Merck Silica gel 60 (40–63 mm, 230–400 mesh) under pressure of air.

Freeze-drying was done on a Leybold-Heraeus, model Lyovac GT 2, apparatus.

Preparation of starting materials 4-aminomethyl-1-(N-benzyloxycarbonylamidino)-benzene (H-Pab(Z))

(i) 4-cyanobenzyl azide

A solution of 20.23 g (0.31 mol) sodium azide in 50 ml water was added to 49.15 g (251 mmol) 4-cyanobenzyl bromide in 200 ml DMF at ambient temperature. An exothermic reaction took place and after 1.5 h the reaction mixture was diluted with 200 ml toluene(caution: In order to avoid separation of potentially explosive azide compounds it is adviseable to add the toluene to the reaction mixture before addition of the water) and 500 ml water. The aqueous phase was extracted with an additional 2×50 ml toluene. The combined organic extracts were washed with 2×50 ml water and brine and finally dried ($MgSO_4$) and filtered.

The solution was used as such in the next step.

$^1$H-NMR (300 MHz, $CDCl_3$); δ 4.4 (s, 2H), 7.4 (d, 2H), 7.7 (d, 2H).

(ii) 4-amidino benzyl azide

Hydrogen chloride was bubbled into a mixture of 250 ml absolute ethanol and the solution from step (i) (approximately 200 ml) above at −5° C. until saturation. Storage at 8° C. for 24 h and evaporation of most of the solvent followed by precipitation by addition of anhydrous ether gave white crystals which were isolated by filtration and dissolved in 1.8 of alcoholic ammonia. After 48 h most of the solvent was removed and 200 ml 3.75M NaOH solution was added whereupon 4-amidino benzyl azide precipitated as colourless crystals. The crystals were isolated by filtration. At this point the yield of 4-amidino benzyl azide was 22.5 g (total 51%).

Ethylimidatobenzyl azide hydrochloride:

¹H-NMR (500 MHz, CD₃OD): δ 1.6 (t, 3H), 4.5 (s, 2H), 4.65 (q, 2H), 4.8 (br s, 2H), 7.6 (d, 2H), 8.1 (d, 2H)

4-amidino benzyl azide:

¹H-NMR (500 MHz, CDCl₃): δ 4.3 (s, 2H), 5.7 (br s, 3H), 7.3 (d, 2H), 7.6 (d, 2H).

¹³C-NMR (125 MHz, CDCl₃): amidine carbon: δ 165.5.

(iii) 4-(benzyloxycarbonylamidino) benzyl azide

The crystals from (ii) above were dissolved in 500 ml methylene chloride and the resulting solution was dried (K₂CO₃), filtered and 27 ml (194 mmol) triethyl amine was added. 25 ml Benzyl chloroformate was slowly added to the stirred solution while the reaction mixture was cooled in an ice bath. After 30 minutes an additional 2 ml benzyl chloroformate was added and stirring was continued for another 30 minutes. Subsequently, water was added and the aqueous phase was adjusted to pH 7 with 2M HCl. The organic phase was dried (MgSO₄) and the solvent was removed in vacuo. 4(benzyloxycarbonylamidino) benzyl azide was finally isolated as colorless crystals from ether/methylene chloride/hexane.

¹H-NMR (500 MHz, CDCl₃): δ 4.4 (s, 2H), 5.3 (s, 2H), 6.3–7.0 (br s, 1H), 7.3–7.4 (m, 5H), 7.5 (d, 2H), 7.9 (d, 2H), 9.3–9.6 (br s, 1H).

¹³C-NMR (125 MHz, CDCl₃): amidine carbon: δ 167.5.

(iv) 4-aminomethyl-1-(N-benzyloxycarbonylamidino)-benzene (H-Pab(Z))

26.3 g (100 mmol) triphenylphosphine was added at room temperature to the 4-(benzyloxycarbonylamidino) benzyl azide from (iii) above dissolved in 160 ml THF. After 16 h an additional 6.6 g (25 mmol) triphenylphosphine was added and the solution was allowed to stand for 4 h before removal of the solvent in vacuo. The residue was dissolved in methylene chloride and extracted with 2M HCl. The aqueous phase was washed with methylene chloride and ether and was subsequently made alkaline with 3.75M sodium hydroxide solution. Extraction with methylene chloride followed by drying (K₂CO₃) and removal of the solvent in vacuo gave 20 g (The total yield starting from cyanobenzyl bromide is 28%) of a yellow oil which solidified on standing.

¹H-NMR (500 MHz, CDCl₃): δ 1.2–2.2 (br s, 2H), 3.8 (s, 2H), 5.2 (s, 2H), 7.2–7.35 (m, 5H), 7.4 (d, 2H), 7.8 (d, 2H), 9.1–9.6 (br s, 1H).

¹³C-NMR (125 MHz, CDCl₃): amidine and carbonyl carbons: δ 164.6 and 168.17.

H-Aze-OMe x HCl

Prepared according to the procedure described by Seebach D. et. al.in Liebigs Ann. Chem., p. 687, 1990.

Boc-(R)Cgl-OH

Boc-(R)-Pgl-OH, 32.6 g (0.13 mol), was dissolved in 300 ml of methanol and 5 g of Rh/Al₂O₃ was added. The solution was hydrogenated at 5.2 to 2.8 MPa for 3 days. After filtration and evaporation of the solvent NMR showed the presence of about 25% of the methyl ester of the title compound. The crude material was dissolved in 500 ml of THF and 300 ml of water and 20 g of LiOH were added. The mixture was stirred overnight and the THF was evaporated. The remaining water phase was acidified with KHSO₄ and extracted three times with ethyl acetate. The combined organic layer was washed with water, dried (Na₂SO₄) and evaporated to give 28.3 g (83%) of the desired product.

¹H-NMR (300 MHZ, CDCl₃): δ 0.9–1.7 (m, 20H), 4.0–4.2 (m, 1H), 5.2 (d, 1H).

Boc-(R)Cgl-Aze-OH (i) Boc-(R)Cgl-Aze-OMe

To a stirred mixture of 3.86 g (15 mmol) Boc-(R)Cgl-OH, 2.27 g (15 mmol) H-Aze-OMe×HCl and 2.75 g (22.5 mmol) DMAP in 40 mL CH₃CN at 5° C. was added 3.16 g (16.5 mmol) EDC. The reaction mixture was stirred at room temperature for 48h. The solvent was evaporated and the residue was dissolved in 150 ml EtOAc and 20 ml H₂O. The separated organic layer was washed with 2×20 ml 0.5 M KHSO₄, 2×10 ml NaHCO₃(saturated), 1×10 ml H₂O, 1×10 ml brine and dried (MgSO₄). Evaporation of the solvent gave 4.91 g (92%) of the title compound which was used without further purification in the next step.

¹H NMR (500 MHz, CDCl₃, 0.1 g/ml): major rotamer, 0.83–1.35 (m, 5H), 1.38 (s, 9H), 1.47–1.84 (m, 6H), 2.18–2.27 (m, 1H), 2.50–2.62 (m, 1H), 3.72 (s, 3H), 3.94–4.06 (m, 1H), 4.07–4.15 (m, 1H), 4.39–4.47 (m, 1H), 4.68 (dd, J=9.1, J=5.1, 1H), 5.09 (d, J=9.2, 1H). Resolved peaks from minor rotamer, 2.27–2.35 (m, 1H), 3.77 (s, 3H), 3.80–3.87 (m, 1H), 3.88–3.95 (m, 1H), 4.92 (d, J=9.2, 1H), 5.21 (dd, J=9.1, J~5, 1H).

(ii) Boc-(R)Cgl-Aze-OH

The hydrolysis of Boc-(R)Cgl-Aze-OMe was carried out according to the procedure described for Boc-(R)Cha-Pic-OEt (vide infra). The product was crystallized from EtOH/acetone/water (1/1/3.95) yield 80%.

¹H-NMR (500 MHz, CDCl₃): δ 0.85–1.3 (m, 5H), 1.40 (s, 9H), 1.5–1.9 (m, 6H), 1.95–2.2 (m, 2H), 3.92 (m, 1H), 4.09 (m, 1H), 4.35 (m, 1H), 4.95 (m, 1H), 5.16 (bd, 1H).

Preparation of the compound HOOC—CH₂—(R)Cgl-Aze-Pab (i) Boc-(R)Cgl-Aze-Pab(Z)

To a stirred mixture of 3.40 g (10 mmol) Boc-(R)CglAze-OH (See Preparation of starting materials) and 5.13 g DMAP (42 mmol) in 120 ml CH₃CN was added 3.18 g H-Pab(Z) ×HCl (See Preparation of starting materials). After stirring for 2 hours at room temperature the mixture was cooled to -8° C. and 2.01 g (10.5 mmol) EDC was added. The reaction was allowed to reach room temperature and the stirring was continued for an additional 47 hours. The solvent was evaporated and the residue was dissolved in 200 ml EtOAc. The organic phase was washed with 1×50 ml water, 1×50+ 2×25 ml 0.5M KHSO₄, 2×25 ml NaHCO₃(saturated), 1×50 ml water and dried. Evaporation of the solvent gave 5.21 g (86%) of the title compound.

¹H-NMR (500MHz, CDCl₃): δ 0.8–1.9 (m, 20H; thereof 1.30 (s, 9H)), 2.35–2.6 (m, 2H), 3.74 (bt, 1H), 4.10 (m, 1H), 4.25–4.4 (m, 2H), 4.45–4.6 (m, 1H, rotamers), 4.75–5.0 (m, 1H, rotamers), 5.08 (bd, 2H), 5.15 (s, 2H), 7.15–7.35 (m, 5H), 7.41 (d, 2H), 7.77 (d, 2H), 8.21 (m, 1H).

(ii) H-(R)Cgl-Aze-Pab(Z)

To a cold (ice bath temperature) solution of 18.8 g HCl(g) in 195 ml EtOAc was added 4.69 g (7.743 mmol) of Boc-(R)Cgl-Aze-Pab(Z) together with 40 ml EtOAc. The reaction mixture was allowed to reach room temperature and stirred for 30 min. 140 ml Et₂O was added to the clear solution where upon a precipitate was formed. The reaction was left at room temperature for an additional 1 h and 40 minutes. The precipitate was filtered off, washed quickly with 150 ml Et₂O and dried in vaccuo. The precipitate was dissolved in 50 ml of water and made alkaline with 15 ml 2M NaOH. The alkaline waterphase was extracted with 1×100+1×50 ml CH₂Cl₂. The combined organic phase was washed with 1×20 ml water, 1×20 ml Brine and dried (MgSO₄). Evaporation of the solvent gave 3.44 g (88%) of the title compound.

¹H-NMR (500MHz, CDCl₃): δ 0.8–2.0 (m, 11H), 2.51 (m, 1H), 2.67 (m, 1H), 3.07 (d, 1H), 4.11 (m, 1H), 4.18 (m, 1H), 4.43 (dd, 1H), 4.53 (dd, 1H), 4.91 (m, 1H), 5.22 (s, 2H), 7.2–7.4 (m, 7H), 7.45 (d, 2H), 8.51 (d, 2H).

7

(iii) BnOOC—CH$_2$—(R)Cgl-Aze-Pab(Z)

1.13 g (2.2 mmol) H-(R)Cgl-Aze-Pab(Z), 0.9 g (2.6 mmol) benzyl-2-(ortho-nitrobenzenesulfonyloxy)acetate ((2-NO$_2$)Ph-SO$_2$—OCH$_2$—COOBn) (See Preparation of starting materials), 0.99 g (5.6 mmol) K$_2$CO$_3$ and 113 ml CH$_3$CN were mixed and heated in a 60° C. oilbath for 3 h. The solvent was evaporated in vacuo. EtOAc was added and the mixture was washed with water, the organic phase was extracted with 1M KHSO4 and this waterphase was washed with EtOAc. The acidic waterphase was made alkaline with 1 N NaOH to pH>8 and extracted with EtOAc. The organic phase was washed with water, dried (Na$_2$SO$_4$), filtered and evaporated in vacuo to give 1.17 g of a residue that was twice subjected to flash chromatography using first CH$_2$Cl$_2$/MeOH(NH$_3$-saturated) 95/5 and then diethylether/MeOH (NH$_3$-saturated) 9/1 as eluents to give 0.525 g (36%) of the title compound.

The alkylation was also carried out using Benzyl-2—(para-nitrobenzenesulfonyloxy)acetate ((4-NO$_2$)Ph-SO$_2$—OCH$_2$-COOBn) (See Preparation of starting materials) using the same procedure as above to give the title compound in 52% yield.

$^1$H-NMR (300MHz, CDCl$_3$): δ 0.85–2.15 (m, 11H), 2.48 (m, 1H), 2.63 (m, 1H), 2.88 (d, 1H), 3.24 (d, 1H), 3.27 (d, 1H), 3.95 (m, 1H), 4.05 (m, 1H), 4.44 (m, 1H), 4.55 (m, 1H), 4.91 (m, 1H), 5.07 (s, 2H), 5.22 (s, 2H), 7.2–7.4 (m, 10H), 7.45 (d, 2H), 7.79 (d, 2H), 8.42 (m, 1H).

(iva) HOOC—CH$_2$—(R)Cgl-Aze-Pab×2 HCl

BnOOC—CH$_2$—(R)Cgl-Aze-Pab(Z), 20 mg (0.031 mmol), was dissolved in 5 ml of methanol. A few drops of chloroform and 5% Pd/C, were added and the mixture was hydrogenated at atmospheric pressure for 1 h. After filtration and evaporation the product was lyophilized from water to give 11 mg (72%) of the title compound.

$^1$H-NMR (500MHz, D$_2$O): δ 1.0–2.0 (m, 11H), 2.10 (m, 1H), 2.44 (m, 1H), 2.82 (m, 1H), 3.90 (s, 2H), 4.09 (d, 1H), 4.4–4.55 (m, 2H), 4.66 (s, 2H), 5.08 (m, 1H), 7.65 (d, 2H), 7.89 (d, 2H).

$^{13}$C-NMR (75.5MHz, D$_2$O): amidine and carbonyl carbons: δ 167.3, 167.9, 169.9 and 172.4.

(ivb) HOOC—CH$_2$—(R)Cgl-Aze-Pab

BnOOC—CH$_2$—(R)Cgl-Aze-Pab(Z) was dissolved in EtOH (99%) and hydrogenated over 5% Pd/C, at atmospheric pressure for 5 hours. Filtration of the catalyst through cellite and evaporation of the solvent gave the title compound in 97% yield.

$^1$H-NMR (500MHz, CD$_3$OD, mixture of two rotamers): major rotamer: δ 1.00–1.12 (m, 1H), 1.13–1.34 (m, 4H), 1.55–1.70 (m, 3H), 1.73–1.85 (m, 2H), 1.94–2.02 (bd, 1H), 2.32–2.42 (m, 1H), 2.54–2.64 (m, 1H), 2.95–3.10 (AB-system plus d, 3H), 4.18–4.25 (bq, 1H), 4.28–4.32 (bq, 1H), 4.43–4.60 (AB-system, 2H), 4.80–4.85 (dd, 1H), 7.48–7.54 (d,2H), 7.66–7.71 (d, 2H). Resolved signals from the minor rotamer appear at δ 0.95 (m), 1.43 (m), 2.24 (m), 2.84 (d), 3.96 (m), 4.03 (m), 7.57 (bd), 7.78 (bd).

$^{13}$C-NMR (125MHz, CD$_3$OD): amidine and carbonyl carbons: δ 168.0, 173.0, 176.3 and 179.0

Preparation of the formulations

Formulation A: HOOC—CH$_2$—(R)Cgl-Aze-Pab (base) 1.1 mg/10 ml sucrose monostearate (S-1570) 1.1 mg/10 ml phosphate buffer (KH$_2$PO$_4$:Na$_2$HPO$_4$) 0.1M pH 7.4 ad 10 ml Formulation B: HOOC—CH$_2$—(R)Cgl-Aze-Pab (base) 1.1 mg/10 ml sucrose monopalmitate (P-1570) 1.1 mg/10 ml phosphate buffer (KH$_2$PO$_4$:Na$_2$HPO$_4$) 0.1M pH 7.4 ad 10 ml Formulations A and B were tested in rat colon segments mounted in Ussing-chambers (described by Artursson et al, Pharm. Research, vol.10 No.8 p 1123–29, (1993)). Samples of the solution on both side of the membranes were withdrawn at different time intervals and were analyzed for the concentration of HOOC—CH$_2$—(R)Cgl-Aze-Pab. The ability to cross the intestinal membrane was tested as an indication of the permeability. The permeability coefficient was calculated using the steady-state appearance rate, dQ/dt of the compound on the serosal side of the segments of the surface area, A, and the initial concentration in the mucosal side, CO, according to the equation Papp=dQ/dt*1/ACO.

The results are shown in FIG. 1. N in the figure indicates the number of rats used. The results indicate that the permeability of the thrombin inhibitor HOOC—CH$_2$—(R)Cgl-Aze-Pab to cross the intestinal membrane into the circulation increase two to threefold compared to the control for both sucrose esters, the monostearate and the monopalmitate. The results thus substantiate the conclusion that the presence of such absorption enhancing agents increases the bioavailability of the therapeutically active agent.

Abbreviations

Aze =(s)-azetidine-2-carboxylic acid cgl =(s)-cyclohexyl glycine

Pab =1-amidino-4-aminomethyl benzene

We claim:

1. A pharmaceutical formulation comprising the therapeutically active compound HOOC—CH$_2$—(R)Cgl-Aze-Pab as such or a stereoisomer thereof or a physiologically acceptable salt thereof and one or more absorption enhancing agents, and optionally a pharmaceutical carrier.

2. A pharmaceutical formulation according to claim 1 wherein the absorption enhancing agent is a surfactant.

3. A pharmaceutical formulation according to claim 2 wherein the surfactant is an alkyl glycoside such as sugar glycoside.

4. A pharmaceutical formulation according to claim 2 wherein the surfactant is a sugar fatty acid ester.

5. A pharmaceutical formulation according to claim 4 wherein the sugar fatty acid ester is sucrose monostearate or sucrose monopalmitate.

6. A pharmaceutical formulation according to claim 1 wherein the absorption enhancing agent is a non-steroidal antiinflammatory drug or a derivative thereof.

7. A pharmaceutical formulation according to claim 1 wherein the absorption enhancing agent is a bile salt.

8. A pharmaceutical formulation according to claim 1 wherein the absorption enhancing agent is a lipid.

9. A pharmaceutical formulation according to claim 1 wherein the absorption enhancing agent is a soap, a fatty acid or a fatty acid derivative of carnitine or a peptide.

10. A pharmaceutical formulation according to claim 1 wherein the absorption enhancing agent is an oil.

11. A pharmaceutical formulation according to claim 1 wherein the absorption enhancing agent is an enamine.

12. A pharmaceutical formulation according to claim 1 wherein the absorption enhancing agent is a chelating agent.

13. A pharmaceutical formulation according to claim 1 wherein the absorption enhancing agent is a phenothiazine.

14. A pharmaceutical formulation according to claim 1 wherein the absorption enhancing agent is a product from Maillard reactions.

15. A pharmaceutical formulation according to claim 1 wherein the absorption enhancing agent is a polymer.

16. A pharmaceutical formulation according to claim 1 wherein the absorption enhancing agent is azone, concanavalin A, phosphate or phosphonate derivative, diethyl maleate or diethylethoxymethylene malonate.

17. A pharmaceutical formulation according to claim 1 wherein the absorption enhancing agent is combination of lipids, a lipid and a phospholipid, a lipid and a bile salt, a lipid and an oil, a lipid and a surfactant, or a lipid and a polymer.

18. A pharmaceutical formulation according to claim 1 wherein the absorption enhancing agent is a combination of surfactants and oils.

19. A pharmaceutical formulation according to any one of the preceding claims wherein the active compound HOOC—$CH_2$—(R)Cgl-Aze-Pab is in the form of the free base.

20. A process for the manufacturing of the pharmaceutical formulation defined in any one of the preceding claims characterized by adding an absorption enhancing agent to a solution of the compound HOOC—$CH_2$—(R)Cgl-Aze-Pab, adjusting the pH by a buffering agent to a therapeutically acceptable pH and mixing all ingredients.

21. A method of treating a patient in need of antithrombotic treatment, comprising administering to said patient an effective amount of a pharmaceutical formulation as defined in any one of the claims 1–19.

22. A method for treatment of thromboembolism which comprises administering to a patient in need of such a treatment an effective amount of a pharmaceutical formulation as defined in any one of the claims 1–19.

* * * * *